United States Patent [19]

Chen et al.

[11] Patent Number: 5,116,868
[45] Date of Patent: May 26, 1992

[54] EFFECTIVE OPHTHALMIC IRRIGATION SOLUTION

[75] Inventors: Chung-Ho Chen; Sumi C. Chen, both of Phoenix, Md.

[73] Assignee: The Johns Hopkins University, Baltimore, Md.

[21] Appl. No.: 346,700

[22] Filed: May 3, 1989

[51] Int. Cl.$^5$ .............................................. A61K 31/22
[52] U.S. Cl. ..................... 514/546; 514/912
[58] Field of Search .............................. 514/546, 912

[56] References Cited

U.S. PATENT DOCUMENTS

| | | | |
|---|---|---|---|
| 4,620,979 | 11/1986 | Schachar | 514/912 |
| 4,663,289 | 5/1987 | Veech | 435/1 |
| 4,695,536 | 9/1987 | Lindstrom et al. | 435/1 |
| 4,865,846 | 9/1989 | Kaufman | 514/912 |
| 4,888,168 | 12/1989 | Potts et al. | 514/912 |

OTHER PUBLICATIONS

Albert L. Lehninger, Principles of Biochemistry, Worth Publishers, Inc., pp. 524-526, 1982.
Olson, Nature 195:597, 1962.
Bassenge et al., Am. J. Physiol, 208:162, 1965.
Owen et al., J. Clin. Invest., 46:1598, 1968.
Hawkins et al., Biochem. J., 122:13, 1971 and 125:541, 1971.
Spenser and Lehninger, Biochem. J., 154:405, 1976.
McCarey and Kaufman, Invest. Ophthalmol., 13:165, 1974.
Lindstrom et al., Arch. Ophthalmol., 95:869, 1977.
Lindstrom et al., Am. J. Ophthalmol., 82:72, 1976.
Krebs, H. A., Essays Biochem., 8:2, 1972.
Veech et al., Biochem. J., 115:609, 1969.
Veech et al., J. Biol. Chem., 254:6538, 1979.
Veech et al., FEBS Letters, 117, Supplement: K65, 1980.
Williamson et al., Biochem. J., 103:514, 1967.
Embase, 5914481 (1985), Stoneburner et al.
Chen et al, "Lactate Transport and Glycolytic Activity in the Freshly Isolated Rabbit Cornea", Archives of Biochemistry and Biophysics, vol. 276, No. 1, Jan., pp. 70-76, 1990.

Primary Examiner—Frederick E. Waddell
Assistant Examiner—Zohreh A. Fay
Attorney, Agent, or Firm—Cushman, Darby & Cushman

[57] ABSTRACT

A composition comprising an aqueous phosphate-buffered balanced salt solution including glucose, an antioxidant, and ketone bodies and/or precursors thereof is disclosed. The disclosed composition is particularly useful as an ophthalmic irrigation solution which may be used in ocular surgery, although other uses, for example, ophthalmic topical application and surgeries in general, are also contemplated.

18 Claims, 3 Drawing Sheets

EFFECTIVE OPHTHALMIC IRRIGATION SOLUTION

BACKGROUND OF THE INVENTION

1. Technical Field

The present invention relates to a novel composition which is particularly useful as an ophthalmic irrigation solution which may be used in ocular surgery, although other uses, for example, ophthalmic topical application and surgeries in general, are also contemplated.

2. Background Information

An ophthalmic irrigation solution is used for the application on the external surface of the eyes topically and in ocular surgeries to rinse, as well as to keep the operated ocular tissues moist. Replacement of the aqueous and/or vitreous humors with the irrigation solution occurs as the consequence of ocular surgeries including corneal transplant (penetrating keratoplasty), cataract extraction, intraocular lens implantation and vitrectomy. In these instances, the irrigation solution remains in the eyes after surgery until the components are either deprived by the surrounding tissues or the solution is eventually equilibrated with body fluids, with subsequent clearance through the circulation. Thus, the irrigation solution used should not only be physiologically compatible, including tonicity and pH, but it should also contain components enabling the cells to sustain their viability and capability to perform physiological functions, at least until a full equilibration of the anterior chamber and the vitreous with the physiological body fluids is reached.

The irrigation solution is of particular importance to the cornea and the lens. Both organs are avascular. The cornea obtains its nourishment mainly from the fluid in the anterior chamber, and to a lesser extent, from the tear. The lens obtains its nourishment from fluids, both in the anterior chamber and in the vitreous. The retina, ciliary body and iris are vascularized tissues; they obtain their nourishment through the circulating plasma of the blood vessel network. Therefore, the components of the irrigation solution may not exert an effect on these tissues as significant as that on the cornea and the lens.

In the cornea, the monolayer endothelium lining the posterior surface contains ion transport sites which help maintain the cornea deturgescense and thereby the transparency. In the lens, the ion transport sites are located in the epithelium underneath the capsule. In general, the $Na^+$-$K^+$ ATPase is located in the cytoplasmic membrane which helps maintain cellular $Na^+$ and $K^+$ contents at approximately 10 and 100 mM, respectively, and facilitates the transport against the extracellular salt concentration gradients of about 120 mM $Na^+$ and 10 mM $K^+$. Adequate energy is needed for the cells (and tissues) to perform the ion transport activity.

Glucose is the major energy source for mammalian cells. The cornea, lens and retina are very active glycolysing tissues which utilize glucose and produce lactic acid, even under aerobic conditions. When the isolated cornea is stored in a medium containing glucose, excess lactic acid is formed and accumulated, resulting in an acidity that subsequently inhibits the metabolic activity of the tissue. In vivo, lactic acid formed in the vascularized tissue is cleared through the circulation, whereas that formed in the avascular cornea and lens is released into the anterior chamber and removed via the clearance mechanism of the circulation. In humans, lactic acid in the anterior chamber is maintained at a steady, low level of approximately 4.0 to 4.5 mM.

Glucose is an important and useful energy source for ocular tissues when it is present in an irrigation solution for in vivo application. Utilization of glucose via glycolysis produces ATP at a high rate and is independent of $O_2$; however, it is not an effective energy-generating pathway, as only 2 moles of ATP are formed per mole of glucose utilized. Two moles of lactic acid are also formed. When the clearance mechanism of the operated ocular tissues is not sufficiently effective, lactic acid will be accumulated, resulting in a lower pH which, in turn, inhibits the metabolic activity of the tissues. In contrast, in tissues with a high mitochondrial population, a complete oxidation of glucose to $CO_2$ and $H_2O$ may occur, via mitochondria, generating as much as 38 moles of ATP per mole of glucose utilized, including the oxidation of two moles of NADH formed in the glycolysis. Therefore, it is evident that utilization of substrates via oxidation in mitochondria is an effective energy-generating pathway when oxygen is available. Under this condition, there is no lactic acid accumulation. In addition, lactic acid accumulation may be diminished or minimized when anaerobic glycolysis is inhibited by an enhanced respiration via the Pasteur effect.

Glucose cannot be used directly as a substrate in the mitochondria; it has to be converted first to pyruvate via glycolysis. Ketone bodies (a collective term for acetone, acetoacetate and $\beta$-hydroxybutyrate) and precursors thereof (such as short chain fatty acids and ketogenic amino acids) are readily oxidized in the mitochondria, producing 32 molecules of ATP per acetyl moiety utilized. Therefore, ketone bodies and precursors thereof are energy-rich or energy-efficient molecules. Furthermore, oxidation of ketone bodies and precursors thereof results in an enhanced respiration which, in turn, inhibits anaerobic glycolysis via the Pasteur effect. In humans and most other mammals, ketone bodies are formed in the liver from oxidation of fatty acids and ketogenic amino acids (including leucine, lysine, phenylalanine, tyrosine and tryptophan). Ketone bodies are not oxidized further in the liver but are transported by the circulating blood to the peripheral tissues. There they are oxidized to $CO_2$ and $H_2O$ via acetyl CoA and citric acid cycle, yielding a rich energy for the peripheral tissues. Ketone bodies are known to be the preferred fuel for the brain, muscle, and kidney during starvation. (R. E. Olson, *Nature*, 195, 597, 1962; E. Bassenge et al, *Am. J. Physiol.*, 208, 162, 1965; O. E. Owen et al, *J. Clin. Invest.*, 46, 1589, 1967; and R. A. Howkins et al, *Biochem. J.*, 122, 13, 1971 and 125, 541, 1971). Ketone bodies are also utilized in the cornea.

In addition, complete oxidation of ketone bodies and precursors thereof yields $CO_2$ and $H_2O$, with accumulation of no other metabolic wastes. Carbon dioxide formed is subsequently hydrated to form carbonic acid, which is further dissociated to form bicarbonate at pH 7.4. Bicarbonate has been suggested as necessary for the ion transport process across the corneal endothelium (S. Hodson et al., *J. Physiol.*, 263, 563, 1976).

Pathways for the formation of ketone bodies from fatty acids and ketogenic amino acids are illustrated in FIG. 1.

SUMMARY OF THE INVENTION

The present invention relates to an ophthalmic irrigation composition comprising an aqueous phosphate-buffered balanced salt solution including glucose, an antioxidant, and ketone bodies and/or precursors thereof.

The present invention also relates to a method of preparing the ophthalmic irrigation composition which comprises mixing together glucose, an antioxidant, and ketone bodies and/or precursors thereof and an aqueous phosphate-buffered salt solution in amounts sufficient to form an ophthalmic irrigation composition that effectively meets the requirements of ocular tissues for efficient physiological and biochemical functioning, as detailed above.

DETAILED DESCRIPTION OF THE INVENTION

Figure 1:
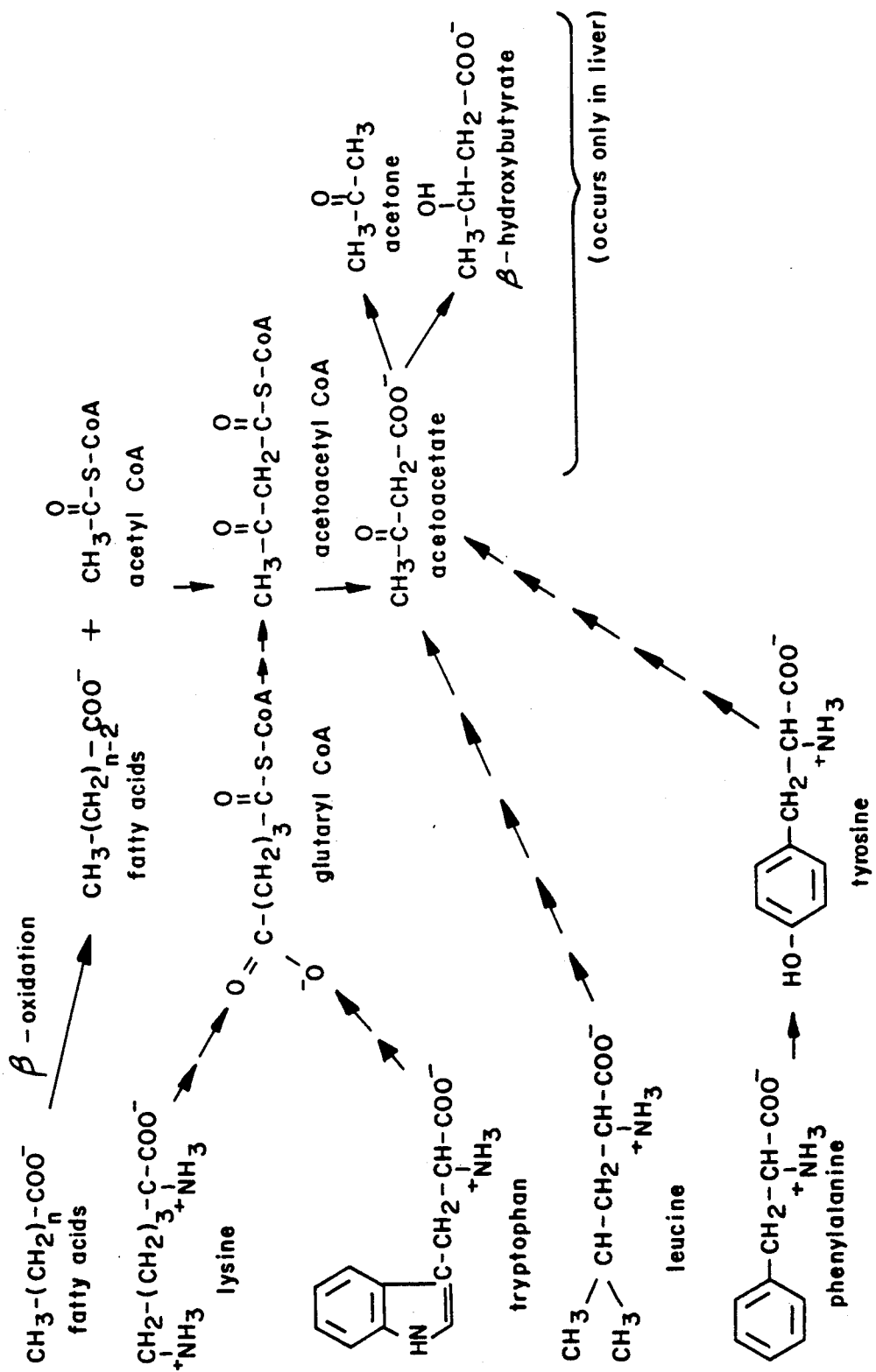
FIG. 1 shows the pathways for the formation of ketone bodies from fatty acids and ketogenic amino acids.

Broadly described, the ophthalmic irrigation composition of the present invention comprises an aqueous phosphate-buffered balanced salt solution including glucose, an antioxidant, and/or ketone bodies and precursors thereof. The composition utilizes certain of the special features of its components, particularly the glucose and ketone bodies and/or precursors thereof as detailed above, so as to effectively meet the requirements of ocular tissues for efficient physiological and biochemical functioning.

The present aqueous phosphate-buffered balanced salt solution containing glucose, an antioxidant, and ketone bodies and/or precursors thereof thus satisfies the minimum essential nutrient requirements of ocular tissues, both with or without high density of mitochondria (or no mitochondria) and of other tissues in general. Ocular tissues irrigated using the present ophthalmic irrigation composition, for example, following surgery, are capable of performing energy-dependent metabolic functions, such as ion transport and protein synthesis, and physiological functions such as maintaining a thin and clear cornea.

The present ophthalmic irrigation composition thus provides, for example, a balanced and rich energy source for the three different tissue layers of the cornea. That is, it satisfies the need for the high respiratory activity of the endothelium, for the high glycolytic activity of the epithelium and the stroma and for the attainment of an essential intracellular energy level for corneal fluid and ion transport.

Typical compositions which are suitable for use as an ophthalmic irrigation solution according to the present invention, including ranges of the components, are summarized in Table 1 below.

TABLE 1

TYPICAL COMPOSITIONS OF THE OPTHALMIC IRRIGATION SOLUTION

| Components | Concentrations | | |
|---|---|---|---|
| | mg/ml | mM | Ranges |
| Sodium Chloride | 5.84 | 100 | 90–110 |
| Dibasic Potassium Phosphate (anhydrate) | 0.87 | 5 | 4–6 |
| Dibasic Sodium Phosphate (heptahydrate) | 1.34 | 5 | 4–6 |
| Sodium Citrate (dihydrate) | 2.94 | 10 | 8–12 |
| Magnesium Chloride (hexahydrate) | 0.20 | 1 | 0.5–1.5 |
| Calcium Chloride (anhydrate) | 0.22 | 2 | 1.5–2.5 |
| Sodium Acetate (anhydrate) | 1.64 | 20 | 15–25 |
| D,L-Sodium β-Hydroxybutyrate | 1.26 | 10 | 10–20 |
| Glucose | 0.99 | 5.5 | 5–5.5 | pH is adjusted to 7.4 with acetic acid.

A typical composition of anions and cations contained in the present ophthalmic irrigation solution is summarized in Table 2 below. The calculated osmolarity of the irrigation solution is within the range of about 340 to about 350 mOsM, and preferably about 344.5 mOsM if all the salts are fully dissociated. The actual osmolarity of the prepared irrigation solution is in the range of about 300 to about 310 mOsM, and preferably in the range of about 305 to about 307 mOsM, and most preferably about 307 mOsM.

TABLE 2

TYPICAL COMPOSITION OF IONS IN THE OPTHALMIC IRRIGATION SOLUTION*

| Ions | Concentrations (mM) |
|---|---|
| $Na^+$ | 170 |
| $K^+$ | 10 |
| $Mg^{2+}$ | 1 |
| $Ca^{2+}$ | 2 |
| $Cl^-$ | 106 |
| Inorganic Phosphate (Pi) | 10 |
| Citrate | 10 |
| Acetate | 20 |
| β-Hydroxybutyrate | 10 |

*Glucose is a neutral molecule and is not included in Table 2.

The method of preparing the ophthalmic irrigation solution of the present invention comprises mixing together glucose, an antioxidant, and ketone bodies and/or precursors thereof and an aqueous phosphate-buffered salt solution in amounts sufficient to form an ophthalmic irrigation composition that effectively meets the requirements of ocular tissues for efficient physiological and biochemical functioning, as detailed above.

Because $Ca^{2+}$ and $Mg^{2+}$ at high concentrations form phosphate salt precipitate, it is preferable that all ingredients except $CaCl_2$ and $MgCl_2$ are dissolved in adequate $H_2O$ first, preferably 90%–95% of total volume. The solution is thoroughly mixed and pH is adjusted to 7.3 to 7.5 with acetic acid. Then, $CaCl_2$ and $MgCl_2$, in 0.5M stock solutions, or in ranges from 0.2 to 1.0M, are added. The pH is checked and adjusted, if necessary, to 7.3 to 7.5, preferably pH 7.4, with 1N acetic acid. Finally, $H_2O$ is added to make up the volume. Preferably, deionized double-distilled $H_2O$ is used for the solution preparation. All the components used should be reagent grade.

A number of variations are possible when preparing the present ophthalmic irrigation solution. Some examples of possible variations are given below.

1. The phosphate buffer can be prepared using dibasic potassium phosphate and monobasic potassium phosphate. In this case, total potassium ions are increased to 15 mM.
2. The phosphate buffer can be prepared using dibasic sodium phosphate and monobasic sodium phosphate. In this case, 8 to 12 mM KCl should be added. An adjustment of Na+ concentration is unnecessary.
3. The phosphate buffer can be prepared using any other phosphate salts and phosphoric acid, with an appropriate titration to pH 7.4. In any case, K+ should have a final concentration of 8 to 12 mM. The pH can vary from 7.3 to 7.5.
4. Sodium acetate can be replaced by a half equivalent amount of D-$\beta$-hydroxybutyrate with 10 mM NaCl for Na+ concentration adjustment, or replaced by an equivalent amount of D,L-$\beta$-hydroxybutyrate with no Na+ concentration adjustment.
5. Sodium acetate can be replaced by one or a combination of ketogenic amino acids, including leucine, lysine, phenylalanine, tryptophan and tyrosine, with a total of 10 mM, or in ranges of 7.5 to 12.5 mM. In this case, 10 mM Na+ is added for Na+ concentration adjustment.
6. One or more ketogenic amino acids at concentrations from 0.1 to 5.0 mM, preferably 1 to 2 mM, can be added as components of the ophthalmic irrigation solution. An equivalent amount of NaCl is subtracted to adjust Na+ concentration.
7. Other short chain fatty acids, such as butyric acid and caproic acid, at 10 mM, or in ranges from 5 to 15 mM, can also be used. However, the low solubility of caproic acid in the aqueous solution may limit its application.
8. Although $\beta$-hydroxybutyrate can be replaced by either acetate or acetoacetate, $\beta$-hydroxybutyrate is preferred. $\beta$-hydroxybutyrate is stable and cost-efficient. It is also readily utilized by the cells, and it is more energy-efficient than acetate. One mole of $\beta$-hydroxybutyrate will generate 64 moles of ATP and one mole of NADH, which can further generate 3 moles of ATP.
9. Citrate is used as an antioxidant, and it is also an energy-generating substrate for the tissues. The ketogenic phenylalanine is also an antioxidant, but with a reduction potential lower than that of citrate. However, with its richness in energy, the supplement of phenylalanine at 2 mM, or in ranges from 0.5 to 3.0 mM, to the ophthalmic irrigation solution is favorable. Other antioxidants, such as vitamin E, cysteine, reduced glutathione and ascorbate, can also be used. However, these antioxidants are not as stable as citrate during storage. Furthermore, if cysteine, reduced glutathione, or ascorbate is used, hydrogen peroxide is elaborated, especially in the presence of $Cu^{2+}$. Therefore, cysteine, reduced glutathione and ascorbate are not favored for inclusion if catalase (at 5 units/ml or greater) is not present. Hydrogen peroxide exerts a cytotoxic effect on the cells.
10. The addition of 1 to 50 units of catalase per ml of ophthalmic irrigation solution is useful, but it is not required. 11.
11. The D-isomer of $\beta$-hydroxybutyrate is a preferred component of the ophthalmic irrigation solution because only D-isomer is utilized in the cells. However, D, L-racemates or D- and L-isomer mixtures are cost-efficient and readily available commercially, and can be used.
12. If necessary, mannitol can be used to adjust the osmolarity of the ophthalmic irrigation solution to a range of about 300 to about 310 mOsM.

The ophthalmic irrigation solution of the present invention is not intended for use as a therapeutic agent. The present irrigation solution, like other irrigation solutions currently available, is formulated with the minimum of essential components for use primarily to enable ocular tissues (or cells) to sustain their viability and capability to perform their physiological functions during the transition period following intraocular surgeries including, for example, corneal transplant, intraocular lens implantation, cataract extraction and vitrectomy. The transition period is defined as the time between surgery and a full equilibration of the solution in the anterior chamber and/or the vitreous with the physiological fluids from the body. As noted above, the present irrigation solution is also useful for ophthalmic topical application and for surgeries in general.

The present composition contains a physiologically compatible salt solution, with concentration ranges similar to those found in blood plasma. According to the present invention, phosphate (typically 10 mM) is used as both a buffer and a substrate for phosphorylation of ADP to form ATP in energy metabolism. Phosphate has a strong buffer capacity at pH 7.4. Bicarbonate is used in other irrigation solutions currently available in the market (such as BSS-plus, manufactured and marketed by Alcon, Fort Worth, Tex.). However, bicarbonate is not utilized as a component in the present composition because, when a bicarbonate buffer is used, the pH of the solution varies with $CO_2$ partial pressure ($P_{CO_2}$). Furthermore, although exogenous bicarbonate is not added, bicarbonate is formed via the respiration (or oxidative phosphorylation) of the tissues in situ. In this process, the substrates are oxidized (in the mitochondria) to form $CO_2$ and $H_2O$. $CO_2$ formed is then hydrated to form $H_2CO_3$, which is rapidly dissociated to form $HCO_3^-$. In the rabbit cornea $CO_2$ is produced at a rate of about 1.3 $\mu$moles/cm/hr. In human corneas, the rate is about 30 to 50% higher.

D-$\beta$-Hydroxybutyrate is readily oxidized in the mitochondria to form acetoacetate and NADH, catalyzed by $\beta$-hydroxybutyrate dehydrogenase. Acetoacetate further reacts with succinyl CoA to form acetoacetyl CoA, which is then further degraded, with the catalysis of thiophorase, to form acetyl CoA. Fatty acids are utilized in the cells via $\beta$-oxidation, to form acetyl CoA. Ketogenic amino acids are also catabolized in the cells to yield acetoacetate or acetoacetyl CoA and then to acetyl CoA. Acetyl CoA from these reactions are then further oxidized to $CO_2$ and $H_2O$ via the citric acid cycle in the mitochondria. Pathways of ketone body formation from fatty acid and ketogenic amino acids are briefly illustrated in FIG. 1. The oxidation of acetyl CoA is an energy-efficient process, 30 moles of ATP and 2 moles of GTP (or a total of 32 moles of ATP) being formed per mole of acetyl CoA utilized. Inorganic phosphate in the irrigation solution provides for oxidative phosphorylation, which is coupled to electron transport, to react with ADP to form ATP.

For glucose consumed in the cornea, about 40% is via glycolysis and 60% via respiration, as may be seen from Table 3 below.

TABLE 3
METABOLIC ACTIVITY IN CORNEAL TISSUE LAYERS

| Tissue Layers | Glucose Consumption Rate ($\mu mol/cm^2/hr$) | $\dfrac{\text{Lactate Formation}}{\text{Pyrurate Oxidation}}$ Ratio |
|---|---|---|
| Epithelium | 0.185 ± 0.019 (48%) | 1:1 |
| Stroma | 0.096 ± 0.013 (25%) | 2:1 |
| Endothelium | 0.107 ± 0.006 (28%) | 1:2 |

Stroma consumes glucose via glycolysis at a rate about twice that of respiration. In the lens, mitochondria are located only in the epithelium. Thus, glucose is an important energy source in these cells, especially the cells in the lens nucleus. In these cells, there are very little or no mitochondria to utilize acetyl CoA. In other ocular tissues, such as the corneal endothelium and photoreceptors, where mitochondrial population is high, ketone bodies and precursors are energy-efficient substrates. In addition, in these cells, acetyl CoA oxidation elicits an enhanced respiration which, in turn, inhibits anaerobic glycolysis via the Pasteur effect.

Thus, the present irrigation solution containing a phosphate-buffered balanced salt solution, glucose, an antioxidant, and ketone bodies and/or precursors thereof satisfies the minimum essential nutrient requirements of ocular tissues, both with or without high density of mitochondria, or no mitochondria, and of other tissues in general.

The ophthalmic irrigation solution can be used as a simplified version, suitable for short term application, of the cornea storage composition disclosed in co-pending application Ser. No. 92,321, filed Sep. 2, 1987, which is incorporated herein by reference. The cornea storage composition of application Ser. No. 92,321 comprises a tissue culture medium suitable for storing corneas but in which undesired lactate production would normally occur and at least one compound selected from the group consisting of short chain fatty acids and ketone bodies capable of inhibiting lactate production by the corneas, the compound being present in an amount sufficient to inhibit lactate production.

According to one embodiment, a cornea storage medium is prepared which is composed of the ophthalmic irrigation solution, minimum essential amino acids and minimum essential vitamins of either Eagle's (*Science*, 130:432, 1959; *Proc. Soc. Exp. Biol. Med.*, 89:362, 1955), Dubelcco's (*Virology*, 8:396, 1959 and 12:185, 1960) Or Daniel's (*Proc. Soc. Exp. Biol. Med.*, 127:919, 1968). Pre-formulated minimum essential amino acids and minimum essential vitamins are commercially available.

In a second embodiment, a cornea storage medium is formulated by replacing the balanced salt solution of a tissue culture medium, such as Medium 199 and Eagle's minimum essential medium with Earle's salts, with the ophthalmic irrigation solution.

In a third embodiment, a cornea storage medium is prepared by replacing the bicarbonate-buffered balanced salt solution of the cornea storage composition of application Ser. No. 92,321 with the phosphate-buffered balanced salt solution of the ophthalmic irrigation solution.

In a fourth embodiment, a more effective cornea storage composition is composed of a formulation of the first, second or third embodiment described above combined with the synergistic composition of co-pending application Ser. No. 1,844, filed Jan. 9, 1987, which is incorporated herein by reference. The synergistic composition of application Ser. No. 1,844 consists essentially of a synergistically effective mixture of Vascular Endothelial Growth Factor (VEGF), uridine, thymidine and serum-derived factor.

In a fifth embodiment, the ophthalmic irrigation solution is combined with the synergistic composition of application Ser. No. 1,844 to compose a formulation for the preparation of tissues for organ transplant, including corneal transplant.

In a sixth embodiment, a cornea storage medium of the first or second embodiment described above is combined with the synergistic composition of application Ser. No. 1,844 to form an irrigation solution for topical application to stimulate endothelial cell regeneration.

In a seventh embodiment, a cornea storage medium of the first or second embodiment described above is combined with the synergistic composition of application Ser. No. 1,844 to form an organ culture medium for application to facilitate corneal endothelium replacement process prior to corneal transplant.

The ophthalmic irrigation solution is prepared by dissolving all ingredients in exact weights as indicated in the formula, except $Ca^{2+}$ and $Mg^{2+}$ salts, in double distilled water with a volume equal to about 95% of total. The pH of the solution is adjusted to 7.4 with either HCl or NaOH, if necessary. Then $Ca^{2+}$ and $Mg^{2+}$ salts are added, followed with double distilled water to end up the volume. The pH is re-checked and adjusted if necessary.

When the ophthalmic irrigation solution is used as part of a formulation, such as in the first, second, fourth, fifth and seventh embodiments described above, it is preferable to first prepare a concentrated stock irrigation solution without $Ca^{2+}$ and $Mg^{2+}$. Then, an exact, calculated volume is measured and combined with another part of the components, and double distilled water is added to make up about 95% of volume. $Ca^{2+}$ and $Mg^{2+}$ are added and the pH is re-checked and re-adjusted, if necessary. The stock solution is preferably two to ten times concentrate, or more preferably, two to five times concentrate. If not used immediately, the stock solution should be sterilized by filtering through 0.22 or 0.45 $\mu m$ filters such as Nalgene (Nalge Co., Rochester, N.Y.), preferably 0.22 $\mu m$ filters. The sterilized solution may be kept at room temperature.

If the irrigation solution is combined with the synergistic composition, $Mg^{2+}$ should be omitted because the synergistic composition has an adequate quantity of $Mg^{2+}$.

The present invention will be illustrated in detail in the following example. This example is included for illustrative purposes and should not be considered to limit the present invention.

EXAMPLE 1

The efficacy of the present ophthalmic irrigation solution as a balanced energy source was compared to BSS and BSS-plus (manufactured by Alcon Laboratories, Inc., Fort Worth, Tex.), two of the most widely used ophthalmic irrigation solutions at the present time. (Reportedly, BSS-plus is more effective than BSS. Oxidized glutathione, a tripeptide, is present in BSS-plus. Glutathione has been suggested as having a beneficial effect on the fluid transport of the cornea according to Dikstein et al., *J. Physiol.* 221, 29-41, 1972.)

The ophthalmic irrigation solution with typical compositions and concentrations shown in Table 1 was used for experiments in this example. Variations in concentrations of these components within the ranges as indicated in Table 1 are similarly effective. However, the osmolarity of the solution should be maintained in the range preferably from about 305 to about 307 mOsM, and most preferably 307 mOsM. Osmolarity may be adjusted with either NaCl or mannitol.

According to the procedure of the experiment, two incisions, each about 2 mm in length, were made in the corneas of 6 cat eyes. A 25-gauge cannula was then placed in the anterior chamber through one of the incisions in each cornea. The present ophthalmic irrigation solution as exemplified by Table 1 above was then infused in the cornea at a rate of about 7 ml/min, at a pressure of about 15 mm Hg. A total of 1 liter of irrigation solution per cornea was infused in each cornea.

For comparative purposes, the identical procedure was performed with the only exception being the replacement of the present ophthalmic irrigation solution with, in one case, BSS, and in another case, BSS-plus.

All corneas were examined at 1, 2 and 6 days following infusion. Endothelial morphism was examined using a specular microscope, and corneal thickness was measured using a digital pachymeter.

Figure 2:
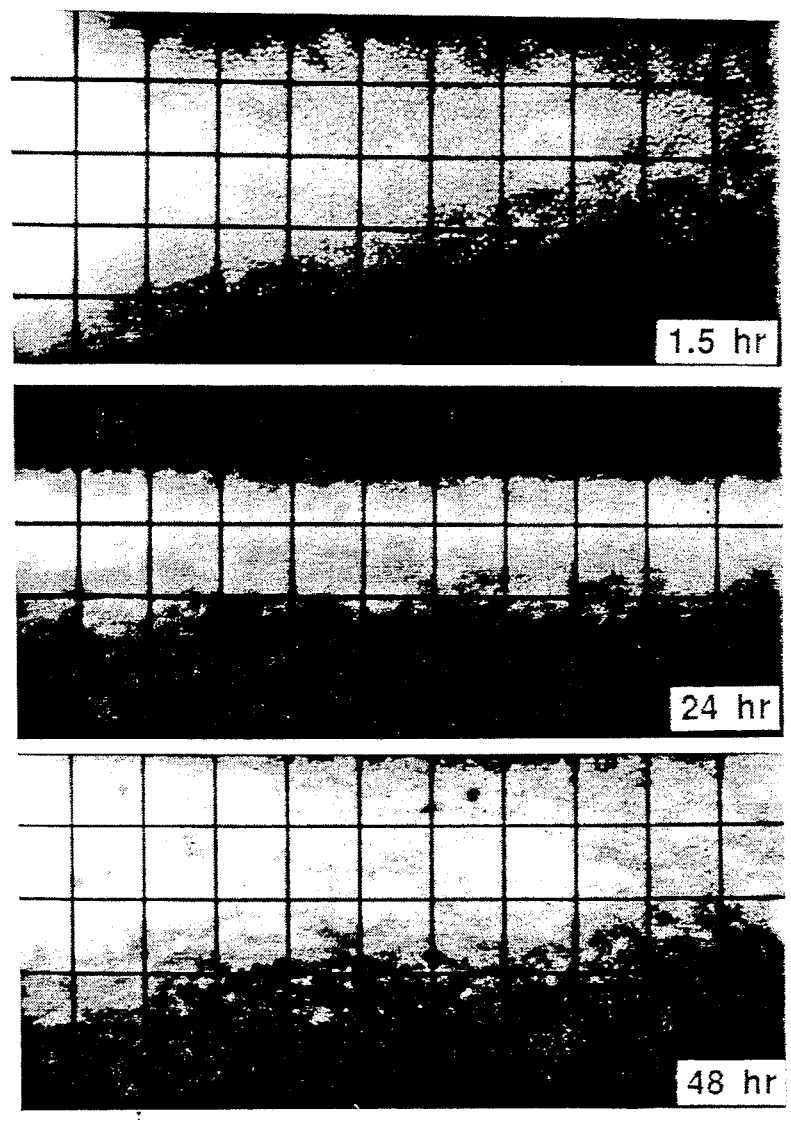
FIG. 2 is a reproduction of a photograph taken by a specular microscope of cat endothelium following anterior chamber irrigation with BSS as described in Example 1.
Figure 3:
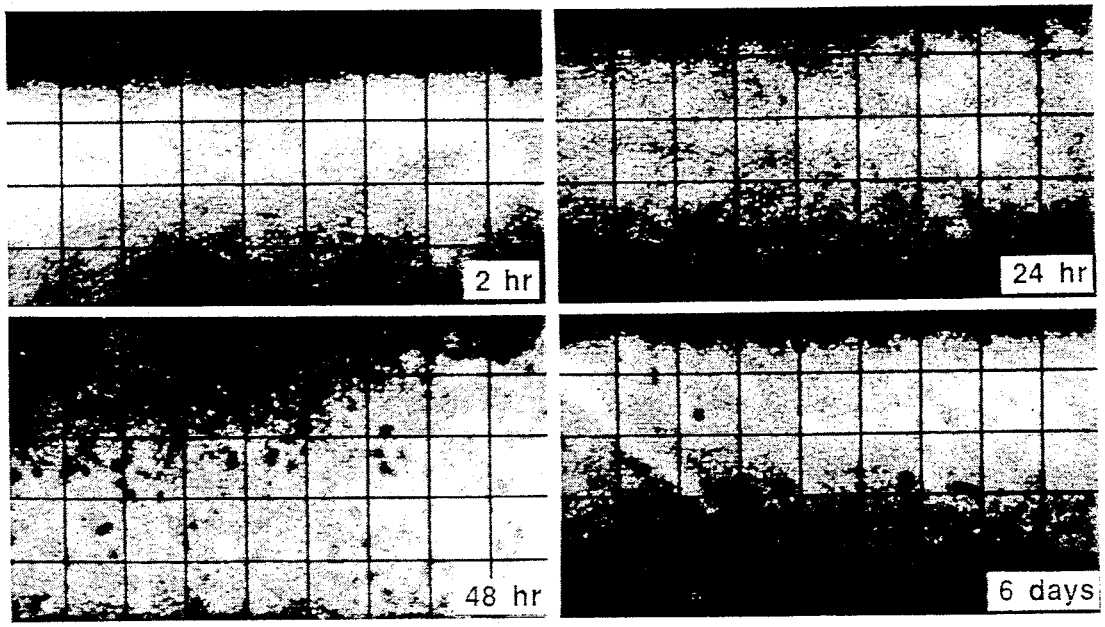
FIG. 3 is a reproduction of a photograph taken by a specular microscope of cat endothelium following anterior chamber irrigation with BSS-plus as described in Example 1.
Figure 4:
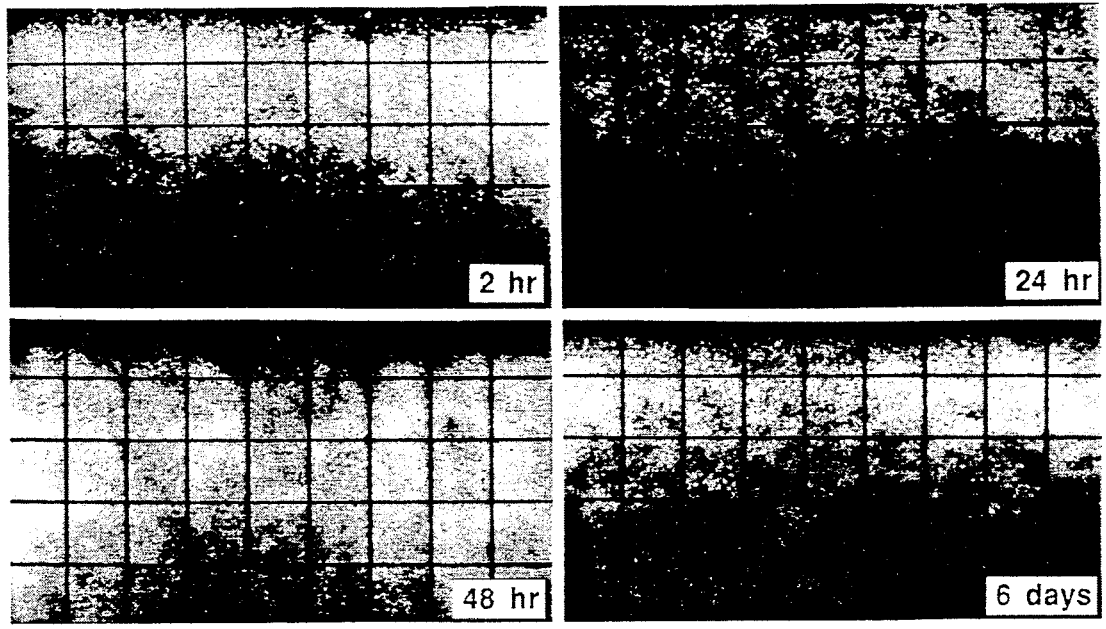
FIG. 4 is a reproduction of a photograph taken by a specular microscope of cat endothelium following anterior chamber ophthalmic irrigation with the ophthalmic irrigation solution described in Example 1.

As shown in FIG. 2, the corneas infused with BSS exhibited extensive endothelial cell losses, endothelial pleomorphism, and corneal swelling on day 1 following infusion. As shown in FIGS. 3 and 4, respectively, on day 1 following infusion with BSS-plus or the present irrigation solution, the shape of endothelial cells remained polygonal (a normal shape), and the corneas were of normal thickness. When examined on day 6 following infusion, the corneas infused with the present ophthalmic irrigation solution (FIG. 4) were comparable or slightly better than those infused with BSS-plus (FIG. 3), in terms of endothelial pleomorphism and corneal thickness.

The above results show that, in terms of maintaining an intact endothelium and a thin and clear cornea, the present irrigation solution is as good as or better than BSS-plus.

It is further noted that in this animal experiment, the continuous infusion of the irrigation solution into the anterior chamber was performed over a period of time much longer than that which takes place in ocular surgery under normal conditions. It is therefore concluded that the present ophthalmic irrigation solution has an efficacious effect on ocular tissues in clinical applications.

In addition to its clinical properties, the present ophthalmic irrigation solution has the following qualities not possessed by other irrigation solutions such as BSS-plus. For example:

1. The present ophthalmic irrigation solution is chemically more stable than BSS-plus, and therefore has a longer shelf-life.
2. The present ophthalmic irrigation solution costs less to manufacture than does BSS-plus.
3. The buffer (phosphate buffer) of the present ophthalmic irrigation solution is stable and has a high capacity. BSS-plus, on the other hand, uses a sodium bicarbonate buffer system, wherein the pH varies with $CO_2$ partial pressure.
4. The present ophthalmic irrigation solution does not require a mixing step prior to application, and therefore, it is easy to use.

While the invention has been described with respect to certain specific embodiments, it will be appreciated that many modifications and changes may be made by those skilled in the art without departing from the spirit of the invention. It is intended, therefore, by the appended claims to cover all such modifications and changes as fall within the true spirit and scope of the invention.

What is claimed is:

1. A method of applying an ophthalmic irrigation composition to ocular tissues to sustain tissue cell viability and capability to perform physiological functions in an amount sufficient to irrigate the tissues, said composition comprising an aqueous phosphate-buffered balanced salt solution including glucose, an antioxidant, and at least one of ketone bodies and precursors thereof in amounts sufficient to effectively meet requirements of ocular tissues for efficient physiological and biochemical functioning.

2. The method of claim 1, wherein the antioxidant is a member of the group consisting of citrate, phenylalanine, vitamin E and ascorbate.

3. The method of claim 2, wherein the antioxidant is citrate.

4. The method of claim 3, wherein the concentration of citrate is in the range of 8-12 mM.

5. The method of claim 1, wherein the ketone bodies are $\beta$-hydroxybutyrate and acetoacetate ions.

6. The method of claim 5, wherein the $\beta$-hydroxybutyrate ions are selected from the group consisting of D-isomers of $\beta$-hydroxybutyrate, and D- and L- racemic mixture of $\beta$-hydroxybutyrate and a D- and L-isomer mixture of $\beta$-hydroxybutyrate.

7. The method of claim 6, wherein the $\beta$-hydroxybutyrate ions are the D-isomers of $\beta$-hydroxybutyrate.

8. The method of claim 5, wherein the concentration of $\beta$-hydroxybutyrate is in the range of 5-10 mM.

9. The method of claim 1, wherein the ketone body precursors are short-chain fatty acids selected from the group consisting of acetic acid and butyric acid, and ketogenic amino acids selected from the group consisting of leucine, lysine, phenylalanine, tyrosine and tryptophan.

10. The method of claim 9, wherein the concentration of the ketone body precursors is in the range of 0.1-10 mM.

11. The method of claim 9, wherein the ophthalmic irrigation solution comprises one ketogenic amino acid having a concentration in the range of 0.1-5.0 mM.

12. The method of claim 9, wherein the ophthalmic irrigation solution comprises one ketogenic amino acid having a concentration in the range of 1-2 mM.

13. The method of claim 9, wherein the ketogenic amino acids have a combined total concentration of in the range of 7.5-12.5 mM.

14. The method of claim 9, wherein the short-chain fatty acids are acetic acid at a concentration in the range of 15-25 mM, or butyric acis at a concentration in the range of 5-15 mM.

15. The method of claim 14, wherein the acetic acid is at a concentration of 20 mM.

16. The method of claim 14, wherein the butyric acid is at a concentration of 10 mM.

17. The method of claim 1, wherein the ophthalmic irrigation composition is applied to the ocular tissues in ocular surgery in an amount sufficient to replace at least one of aqueous humor and vitreous humor with the irrigation solution.

18. The method of claim 1 wherein the pH of the ophthalmic irrigation composition is adjusted to 7.3 to 7.5.

* * * * *